US007411084B2

(12) United States Patent
Bernadino

(10) Patent No.: US 7,411,084 B2
(45) Date of Patent: Aug. 12, 2008

(54) METHOD OF PREPARING PHENOXY ALKANOIC, ALKENOIC, AND ALKYNOIC ACIDS AND SALTS THEREOF VIA A DICARBOXYLATE INTERMEDIATE

(75) Inventor: Joseph N. Bernadino, Stamford, CT (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 417 days.

(21) Appl. No.: 10/489,727

(22) PCT Filed: Sep. 26, 2002

(86) PCT No.: PCT/US02/30671

§ 371 (c)(1),
(2), (4) Date: Apr. 7, 2004

(87) PCT Pub. No.: WO03/026582

PCT Pub. Date: Apr. 3, 2003

(65) Prior Publication Data

US 2004/0171865 A1 Sep. 2, 2004

Related U.S. Application Data

(60) Provisional application No. 60/325,657, filed on Sep. 26, 2001.

(51) Int. Cl.
C07C 69/76 (2006.01)
(52) U.S. Cl. .............................. 560/76; 560/8; 560/19; 560/51; 560/55; 560/81; 560/82
(58) Field of Classification Search ........................ None
See application file for complete search history.

(56) References Cited

U.S. PATENT DOCUMENTS

| 4,337,267 | A | | 6/1982 | Eistetter et al. | |
|---|---|---|---|---|---|
| 5,025,031 | A | | 6/1991 | Lo et al. | |
| 5,192,785 | A | * | 3/1993 | Lo et al. | 514/399 |
| 5,747,537 | A | | 5/1998 | Gordon et al. | |
| 2001/0007875 | A1 | | 7/2001 | Moinet et al. | |

FOREIGN PATENT DOCUMENTS

| DE | 4012405 C1 | 8/1991 |
|---|---|---|
| WO | 97/47612 | 12/1997 |
| WO | WO-01/32596 A1 | 5/2001 |

OTHER PUBLICATIONS

Osmo E. O. Hormi et al. Journal of Organic Chemistry 1987, 52, 5272-5274.*
Maitland Jones, Jr. "Organic Chemistry" 1997, W.W. Norton & Company.*
Mhenni et al. Bulletin de la Societe Chimique de France 1989 (Nov.-Dec.), 824-829; see attached CASREACT abstract.*
Database CA 'Online! Chemical Abstracts Service, Columbus, Ohio, US; Dobrowlska, Ewa et al: "Synthesis of ethyl esters of 2,4-D homologues with a straight carbon chain" XP002358391 retrieved from STN Database accession No. 1964:9471 *abstract* & Przemysl Chemiczny, 42(10), 556-60 CODEN: PRCHAB; ISSN: 0033-2496, 1963.
Naka, Kensuke et al: "Molecular Harpoons. Membrane-Disruptive Surfactants That Can Recognize Osmotic Stress In Prospholipid Bilayers" Journal of the American Chemical Society, 115(6), 2278-86 CODEN: JACSAT; ISSN: 0002-7863, 1993, XP002358379 *p. 2284, col. 2—p. 2285, col. 1; scheme II*.
Kishore, Nandini S. et al: "The Substrate Specificity of Saccharomyces cerevisiae Myristoyl-CoA: Protein N-Myristoyltransferase. Analysis of myristic acid analogs containing oxygen, sulfur, double bonds, triple bonds, and/or an aromatic residue" Journal of Biological Chemistry, 266(14), 8835 CODEN: JBCHA3; ISSN: 0021-9258, 1991, XP002358380 *p. 8853, col. 1*.
Abraham, D.J. et al: "Design, Synthesis, and Testing of Potential Antisickling Agents. 4. Structure-Activity Relationships of Benzyloxy and Phenoxy Acids" Journal of Medicinal Chemistry, 27(8), 967-78 CODEN: JMCMAR; ISSN: 0022-2623, 1984, ZP 002358381 *p. 997, col. 1; table 3; compound 52*.
Wan, A.S.C. et al: "Long-Acting Contraceptive Agents: Norethisterone Esters of Arylcarboxylic Acides" Steroids, 41(3), 309-20 CODEN: STEDAM; ISSN 0039-128X, 1983, XP008057089 *p. 316-317*.
Strube, Michael et al: "Synthesis of DL-2-amino-4-(aryloxy)butanoic acids—analogs of herbicidal aryloxybutanoic acids" Polish Journal of Chemistry, 55(3), 687-93 CODEN: PJCHDQ; ISSN: 0137-5083, 1981, XP008057148 *the whole document*.
Lehman, M.R. et al: "Quaternary Ammonium Salts From Halogenated Alkyl Dimethylamines. III. Omega-Bromo-Heptyl-, -Octyl-, -Nonyl- and Decyl-dimethylamines" Journal of the American Chemical Society, 55, 1977-81 CODEN: JACSAT; ISSN: 0002-7863, 1933 XP002358382 *p. 1978-1979; table 1*.
Littmann, E.R. et al: "Cyclic Quaternary Ammonium Salts from Halogenated Aliphatic Tertiary Amines" Journal of the American Chemical Society, 52, 287-94 CODEN: JACSAT; ISSN: 0002-7863, 1930, XP002358383 *p. 290*.
Carter, Albert S.: "Synthesis of Heptane Dicarboxylic Acid-1,5" Journal of the American Chemical Society, 50, 1967-70 CODEN: JACSAT; ISSN: 0002-7863, 1928, XP002358384 *p. 1968*.
Marvel, C.S. et al: "Synthesis of Some Possible Precursors of Lysine" Journal of the American Chemical Society, 46, 2838-42 CODEN: JACSAT; ISSN: 0002-7863, 1924, XP002358385 *p. 2839-2841*.

(Continued)

*Primary Examiner*—Yvonne Eyler
*Assistant Examiner*—Yevegeny Valenrod
(74) *Attorney, Agent, or Firm*—Darby & Darby, P.C.

(57) ABSTRACT

The present invention relates to a method of preparing a phenoxy alkanoic, alkenoic, or alkynoic acid or a salt thereof from a phenoxy containing compound via a dicarboxylate intermediate. The phenoxy alkanoic, alkenoic, and alkynoic acids and salts thereof prepared by this method are suitable for use in composition for delivering active agents via oral or other routes of administration to animals. Furthermore, the present invention relates to phenoxy dicarboxylic acids and their salts for delivering active agents, such as biologically or chemically active agents, to a target.

18 Claims, No Drawings

OTHER PUBLICATIONS

Gaimster, K.: "Plant Growth Substances: ω-Aryl- and ω-Aryloxy-Alkylcarboxylic Acids" Journal of the Science of Food and Agriculture, 7, 320-9 CODEN: JSFAAE; ISSN: 0022-5142, 1956, XP008057245 *p. 326*.

Renfrew, Andrew H. et al: The reaction of hydroquinones and monosubstituted hydroquinones with dimethyl chloromalonate: Journal of the Chemical Society, Perkin Transactions 1: Organic and Bio-Organic Chemistry (1972-1999), (10), 2382-6 CODEN: JCPRB4; ISSN: 0300-922X, 1979, XP008057111 *p. 2384, col. 2-p. 2385, col. 1*.

Powell, S.G. et al: "Comparison of the activity of certain unsaturated groups with the activity of the allyl group in certain ethers" Journal of the American Chemical Society, 42, 646-58 CODEN: JACSAT; ISSN: 0002-7863, 1920, XP002358386, p. 652.

Hoffmann, F. et al: "Crystal and molecular structures of diethyl 6-'4-(4'-nitrophenylazo)phenoxyl hexylmalonate and its 2'-nitrophenyl isomer" Molecular Cyrstals and Liquid Crystals Science and Technology, Section A: Molecular Crystals and Liquid Crystals, 258, 27-36 CODEN: MCLCE9; ISSN: 1058-725X, 1995, XP008057192 *p. 28*.

Kawashima, Yutaka et al: "Structure-Activity Studies of 3-Benzoylpripionic Acid Derivatives Suppressing Adjuvant Arthritis" Chemical & Pharmaceutical Bulletin, 40(3), 774-7 CODEN: CPBTAL; ISSN: 0009-2363, 1992, XP002024763 *p. 775*.

Sohda, Takashi et al: "Studies on Antidiabetic Agents. II. Synthesis of 5-[4-(1-Methylcyclohexylmethoxy)-benzyl]thiazolidine-2,4-dione (ADD-3878) and its Derivatives." Chemical & Pharmaceutical Bulletin, 30(10), 3580-600 CODEN: CPBTAL, ISSN: 0009-2363, 1982, XP008057136 *p. 3582*.

Matsumura, Noboru et al: "Synthesis and Properties of Novel Macrocyclic Compounds Bearing Thiourea Moieties Using Hypervalent Sulfur" Journal of Heterocyclic Chemistry, 39(1), 189-202 CODEN: JHTCAD; ISSN: 0022-152X, 2002, XP008057115 *p. 195, col. 2*.

McNaught A.D. et al: "leaving group", Compendium of Chemical Terminology. International Union of Pure & Applied Chemistry (IUPAC) Recommendations, Oxford, Blackwell Scientific, GB 1997, XP002426786.

* cited by examiner

US 7,411,084 B2

METHOD OF PREPARING PHENOXY ALKANOIC, ALKENOIC, AND ALKYNOIC ACIDS AND SALTS THEREOF VIA A DICARBOXYLATE INTERMEDIATE

This application claims the benefit of U.S. Provisional Application No. 60/325,657, filed Sep. 26, 2001, which is hereby incorporated by reference.

FIELD OF THE INVENTION

The present invention relates to a method of preparing a phenoxy alkanoic, alkenoic, or alkynoic acid or a salt thereof from a phenoxy containing compound via a dicarboxylate intermediate. The phenoxy alkanoic, alkenoic, and alkynoic acids and salts thereof prepared by this method are suitable for use in compositions for delivering active agents via oral or other routes of administration to animals. Furthermore, the present invention relates to phenoxy dicarboxylic acids and their salts for delivering active agents, such as biologically or chemically active agents, to a target.

BACKGROUND OF THE INVENTION

International Publication No. WO 01/32596 discloses phenoxy alkanoic, alkenoic, and alkynoic acids and salts thereof for the delivery of active agents and methods for preparing the same.

Alternate methods of producing phenoxy alkanoic, alkenoic, and alkynoic acids and salts thereof would be useful, especially where raw materials are expensive, yields are low, and reaction conditions are difficult.

Therefore, there is a need for simpler and less expensive methods of preparing phenoxy alkanoic, alkenoic, and alkynoic acids and salts thereof.

SUMMARY OF THE INVENTION

The present invention relates to a method of preparing a phenoxy alkanoic, alkenoic, or alkynoic acid or a salt thereof from a phenoxy containing compound via a dicarboxylated phenoxy containing intermediate.

The present invention includes a dicarboxylated intermediate having the formula

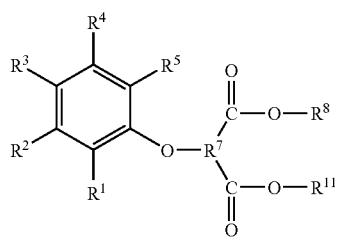

where $R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)$R^{12}$, —NO$_2$, —NR$^9$R$^{10}$, or —N$^+$R$^9$R$^{10}$R$^{13}$(R$^{14}$)$^-$;

$R^5$ is H, —OH, —NO$_2$, halogen, —CF$_3$, —R$^{15}$R$^{16}$, —N$^+$R$^{15}$R$^{16}$R$^{17}$ (R$^{18}$)$^-$, amide, $C_1$-$C_{12}$ alkoxy, $C_1$-$C_{12}$ alkyl, $C_2$-$C_{12}$ alkenyl, carbamate, carbonate, urea, or —C(O)R$^{19}$;

$R^7$ is a linear or branched, $C_1$-$C_{20}$ alkylene, $C_2$-$C_{20}$ alkenylene, or $C_2$-$C_{20}$ alkynylene;

$R^7$ is optionally substituted with $C_1$-$C_4$ alkyl, $C_1$-$C_4$ alkenyl, oxygen, nitrogen, sulfur, halogen, —OH, $C_1$-$C_4$ alkoxy, aryl, heteraryl, or vinyl;

$R^7$ is optionally interrupted with aryl, heteroaryl, vinyl, oxygen, nitrogen, or sulfur;

$R^8$ and $R^{11}$ are independently $C_1$-$C_4$ alkyl or $C_1$-$C_4$ haloalkyl;

$R^9$, $R^{10}$, and $R^{13}$ are independently H or $C_1$-$C_{10}$ alkyl;

$R^{12}$ is H, $C_1$-$C_4$ alkyl, $C_2$-$C_4$ alkenyl, or —NH$_2$;

$R^{14}$ and $R^{18}$ are independently a halide, hydroxide, sulfate, tetrafluoroborate, or phosphate;

$R^{15}$, $R^{16}$, and $R^{17}$ are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, —C(O)R$^{20}$;

$R^{19}$ is —H, $C_1$-$C_6$ alkyl, or $C_2$-$C_{12}$ alkenyl; and $R^{20}$ is —OH, $C_1$-$C_{10}$ alkyl, or $C_2$-$C_{12}$ alkenyl.

According to one preferred embodiment, $R^1$, $R^2$, $R^3$, $R^4$, and $R^5$ are independently hydrogen, hydroxy, halogen, and $C_1$-$C_4$ alkoxy; $R^7$ is a linear or branched, $C_1$-$C_{20}$ alkylene, $C_2$-$C_{20}$ alkenylene, or $C_2$-$C_{20}$ alkynylene; $R^7$ is optionally substituted with $C_1$-$C_4$ alkyl, $C_1$-$C_4$ alkenyl, oxygen, nitrogen, sulfur, halogen, —OH, $C_1$-$C_4$ alkoxy, aryl, heteraryl, or vinyl; $R^7$ is optionally interrupted with aryl, heteroaryl, vinyl, oxygen, nitrogen, or sulfur; and $R^8$ and $R^{11}$ are independently $C_1$-$C_4$ alkyl or $C_1$-$C_4$ haloalkyl.

According to another embodiment, $R_1$, $R^2$, $R^3$, $R^4$, and $R^5$ are selected from hydrogen, hydroxy, halogen, methoxy and ethoxy. According to yet another embodiment, $R^7$ is a $C_7$-$C_{12}$ alkylene and, more preferably, is a linear $C_7$-$C_{12}$ alkylene.

The dicarboxylated intermediate may be prepared by alkylating a phenoxy containing compound with a dicarboxylate alkylating agent. In one embodiment, the phenoxy alkanoic, alkenoic, or alkynoic acid is prepared by hydrolyzing the dicarboxylated intermediate. In another embodiment, the phenoxy alkanoic, alkenoic, or alkynoic acid is prepared by decarboxylating the dicarboxylated intermediate. Optionally, the dicarboxylated intermediate can be hydrolyzed before or after being decarboxylated. Preferably, the dicarboxylated intermediate is hydrolyzed before undergoing decarboxylation. The phenoxy alkanoic, alkenoic, and alkynoic acids and salts thereof prepared by this method are suitable for use in compositions for delivering active agents via oral or other routes of administration to animals.

Many of the alkylating agents disclosed in the prior art, such as ethyl 8-bromo-octanoate as disclosed in International Publication No. WO 01/32596, which is hereby incorporated by reference, are prepared from the dicarboxylate alkylating agents of the present invention. The process for converting the dicarboxylate compounds to the alkylating agents of the prior art is often expensive and time consuming. For example, ethyl 8-bromo-octanoate is prepared from 2-(6-bromohexyl)malonic acid diethyl ester by a multi-step process which includes an expensive distillation step. The process of the present invention reduces the number of synthetic steps required to prepare alkylated salicylamides and, therefore, reduces their manufacturing cost and time.

The present inventors have also discovered that dicarboxylic compounds having the formula

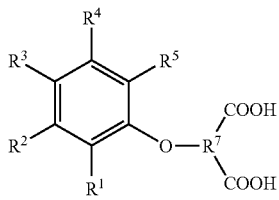

and salts thereof, wherein $R^1$, $R^2$, $R^3$, $R^4$, $R^5$, and $R^7$ are defined as above, facilitate the delivery of active agents. According to a preferred embodiment, $R^7$ is $-(CH_2)_n-$, where n is 4 to 10 and more preferably 7 to 9. The terms "delivery agents" and "delivery agent compounds" as used herein refer to the dicarboxylic compounds of the present invention and phenoxy alkanoic, alkenoic, and alkynoic acids and salts thereof prepared by the method of the present invention.

One embodiment is a composition comprising at least one of the delivery agent compounds and at least one active agent. These compositions deliver active agents to biological systems in increased or improved bioavailability of the active agent compared to administration of the active agent without the delivery agent compound.

Also provided are dosage unit forms comprising the compositions. The dosage unit may be in the form of a liquid or a solid, such as a tablet, capsule or particle, including a powder or sachet.

Another embodiment is a method for administering an active agent to an animal in need of the active agent, by administering a composition comprising at least one of the delivery agent compounds and the active agent to the animal. Preferred routes of administration include the oral, intracolonic and pulmonary routes.

Yet another embodiment is a method of treating a disease or for achieving a desired physiological effect in an animal by administering the composition of the present invention.

Yet another embodiment is a method of preparing a composition of the present invention by mixing at least one delivery agent compound and at least one active agent.

DETAILED DESCRIPTION OF THE INVENTION

The terms "alkyl", "alkenyl", and "alkynyl" (and also "alkylene", "alkenylene", and "alkynylene") as used herein include linear and branched alkyl, alkenyl, and alkynyl substituents, respectively.

The term "substituted" as used herein refers to compounds substituted with one or more of $C_1$-$C_4$ alkyl, $C_2$-$C_4$ alkenyl, and $C_2$-$C_4$ alkynyl.

The term "phenoxy" as used herein refers to a moiety which contains a phenyl group bound to an oxygen atom. The phenyl group may be substituted or unsubstituted.

Preferably, the oxygen atom of the phenoxy group of the phenoxy containing compound is bound to a leaving group. Suitable phenoxy containing compounds include, but are not limited to, compounds having the formula

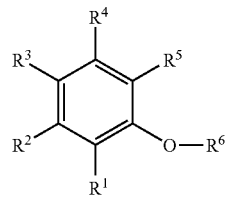

where
$R^1$, $R^2$, $R^3$, $R^4$, and $R^5$ are defined as above; and
$R^6$ is a leaving group (e.g., H).

An example of a suitable phenoxy containing compound is 1,4-dihydroxybenzene.

Alkylation

The phenoxy containing compound is alkylated with a dicarboxylate alkylating agent to form the dicarboxylated intermediate. Suitable dicarboxylate alkylating agents include, but are not limited to, those having the formula

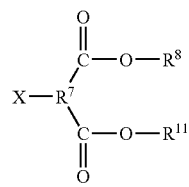

where
$R^7$ is a linear or branched, $C_1$-$C_{20}$ alkylene, $C_2$-$C_{20}$ alkenylene, or $C_2$-$C_{20}$ alkynylene;
$R^7$ is optionally substituted with $C_1$-$C_4$ alkyl, $C_1$-$C_4$ alkenyl, oxygen, nitrogen, sulfur, halogen, $-OH$, $C_1$-$C_4$ alkoxy, aryl, heteraryl, or vinyl;
$R^7$ is optionally interrupted with aryl, heteroaryl, vinyl, oxygen, nitrogen, or sulfur;
$R^8$ and $R^{11}$ are independently $C_1$-$C_4$ alkyl or $C_1$-$C_4$ haloalkyl; and
X is a suitable leaving group.

Suitable leaving groups include, but are not limited to, halogens and alcohols. Two preferred leaving groups are chlorine and bromine. Preferably, $R^8$ and $R^{11}$ are independently $C_1$-$C_4$ alkyl. Preferably, $R^8$ and $R^{11}$ are the same. $R^7$ is preferably $C_4$-$C_{12}$ alkylene and more preferably $C_7$-$C_9$ alkylene.

A preferred dicarboxylate alkylating agent has the formula

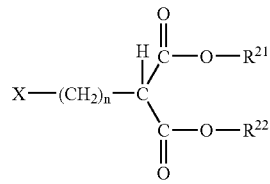

where
$R^{21}$ and $R^{22}$ are independently $C_1$-$C_4$ alkyl;
X is a suitable leaving group; and
n is an integer from 2 to 12.

Preferably, n ranges from 3 to 10, more preferably from 4 to 8, and most preferably from 6 to 8. Non-limiting examples of dicarboxylate alkylating agents include 2-(6-bromohexyl)-malonic acid diethyl ester and 2-(8-bromooctyl)malonic acid diethyl ester, which are available from Allied Signal, Inc. of Morristown, N.J.

Many of the alkylating agents disclosed in the prior art, such as ethyl 8-bromo-octanoate as disclosed in International Publication No. WO 01/32596, are prepared from the dicarboxylate alkylating agents of the present invention. The process for converting the dicarboxylate compounds to the alkylating agents of the prior art is often expensive and time consuming. For example, ethyl 8-bromo-octanoate is prepared from 2-(6-bromohexyl)malonic acid diethyl ester by a multi-step process which includes an expensive distillation step. The process of the present invention reduces the number of synthetic steps required to prepare alkylated salicylamides and, therefore, reduces their manufacturing cost and time.

The reaction between the dicarboxylate alkylating agent and the phenoxy containing compound is preferably carried out in the presence of a slight molar excess of phenoxy containing compound relative to dicarboxylate alkylating agent. Generally, the molar ratio of phenoxy containing compound to dicarboxylate alkylating agent ranges from about 1:1 to about 1:0.5, preferably from about 1:0.99 to about 1:0.8, and most preferably about 1:0.95.

The alkylating reaction is preferably performed in the presence of a suitable base, such as pyridine, picoline, tetramethylguanidine, triethylamine, diisopropylethylamine, sodium or potassium bicarbonate, sodium or potassium carbonate, or any combination of any of the foregoing. According to a preferred embodiment, the base is sodium carbonate. Generally, the reaction is performed in the presence of a slight molar excess of base relative to the phenoxy containing compound.

The reaction may be carried out in solvents including, but not limited to, dimethylacetamide (DMAC); dimethylformamide (DMF); ketones, such as acetone, methylethylketone, and methylisobutylketone; and any combination of any of the foregoing. Preferably, the solvent is non-aqueous.

The alkylating reaction is generally performed at a temperature of from about 40 to about 80° C. The reaction is preferably performed at a temperature of from about 60 to about 80° C. and most preferably at about 70° C. The reaction is typically performed at atmospheric pressure to full vacuum and preferably from about 22 to about 24" Hg of vacuum.

The reaction mixture prior and during the reaction preferably contains less than 5%, more preferably less than 3%, and most preferably less than 1% by weight of water, based upon 100% total weight of reaction mixture.

The reaction is generally performed for a time sufficient to ensure the complete reaction of the alkylating agent. The reaction duration may vary depending on the starting materials. Generally, the reaction is allowed to run for a time sufficient so that at least about 90% and preferably at least about 99% of the limiting reagent, i.e., the dicarboxylate alkylating agent, has been consumed, but is stopped before significant side reaction product builds up. This reduces or eliminates the need for purification of the final product. According to one embodiment, the reaction is performed for from about 2 to about 18 hours, more preferably from about 3 to about 5 hours, and most preferably about 4 hours.

The dicarboxylated intermediate has the formula

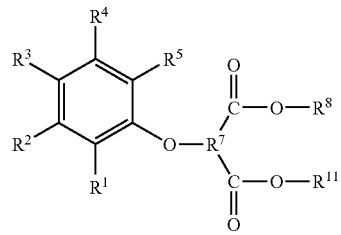

where $R^1, R^2, R^3, R^4, R^5, R^7, R^8$ and $R^{11}$ are defined as above.

The dicarboxylated intermediate is then, optionally, hydrolyzed and decarboxylated to yield the phenoxy alkanoic, alkenoic, or alkynoic acid or salt thereof. The hydrolysis step may be performed before or after the decarboxylation. According to a preferred embodiment, the decarboxylation is performed after hydrolysis. Typically, this process entails the removal of one of the carboxylate moieties. Optionally, the carboxylate moiety or moieties of the alkylated phenoxy containing compound may be hydrolyzed to form a carboxylic acid moiety or carboxylic acid moieties or carboxylate salt. One of the carboxylate groups may be removed and the remaining carboxylate group may be hydrolyzed by acidic, basic and/or neutral hydrolysis as known in the art. Neutral hydrolysis may be performed, for example, with super-heated water at a temperature of from about 100 to about 250° C.

Hydrolysis

Optionally, the phenoxy alkanoic, alkenoic, or alkynoic acid or carboxylate derivative thereof may be further reacted to modify the end group of the alkylating moiety, i.e., $R^8$ or $R^{11}$. For example, the end group —CN or —C(O)O—CH$_2$—CH$_3$ may be modified to —COOH or a salt thereof. This maybe accomplished by methods known in the art, such as neutralization and acidic, basic, and neutral hydrolysis.

Decarboxylation

If a monocarboxylic phenoxy containing compound is desired, the prepared dicarboxylate intermediate may be decarboxylated. The decarboxylation step is performed either before or after the optional hydrolysis step. Preferably, decarboxylation is performed after the deprotecting and deactivating steps and optional hydrolysis step.

The decarboxylation step removes one of the carboxylate moieties from the dicarboxylated intermediate (i.e. one of the two carboxyl groups at the end of the chain $R^7$). Decarboxylation can be performed by any method known in the art, such as acidic hydrolysis. Acidic hydrolysis may be performed, for example, with aqueous hydrochloric acid or aqueous trifluoroacetic acid. For example, acidic hydrolysis may be performed with aqueous hydrochloric acid in acetone at a temperature of from about 25 to about 65° C. According to one embodiment, acidic hydrolysis is performed at a pH of about 3.5 to 4.5 and preferably at about 4. In order to control foaming due to the release of carbon dioxide, the reaction may be performed in the presence of acetone.

Decarboxylation can also be performed by heating the dicarboxylated intermediate in a high boiling point organic solvent, such as xylenes, toluene, heptane, dimethyl acetamide (DMA or DMAC), dimethyl formamide (DMF), methyl sulfoxide, isoparaffins (e.g. isopar-G, isopar-H, isopar-L, and isopar-K available from Exxon Chemicals of Houston, Tex.), and any combination of the foregoing. The organic solvent preferably has a boiling point of at least 110° C. and more preferably of at least 140° C. According to one embodiment, the decarboxylation reaction is preferably performed at a temperature ranging from about 120 to about 160° C., more preferably from about 140 to about 160° C., and most preferably from about 145 to about 165° C. The temperature at which the reaction is performed should be sufficient to remove one of the carboxylate groups at the end of the chain $R^7$.

Preferably, any water in the reaction mixture is removed prior to heating. Water may be removed from a reaction mixture containing the free acid of the dicarboxylated intermediate (which is formed if the dicarboxylated intermediate is hydrolyzed as described in the "Hydrolysis" section above) as follows. The free acid is mixed with an organic solvent in which it is soluble, such as xylenes. The aqueous layer is then extracted, which in this case is the lower layer, leaving the free acid in xylenes. The reaction mixture may then be heated to decarboxylate the free acid of the dicarboxylated intermediate.

The reaction mixture prior and during the decarboxylation reaction preferably contains less than 5%, more preferably less than 3%, and most preferably less than 1% by weight of water, based upon 100% total weight of reaction mixture.

The decarboxylation step may also be performed neat (i.e. without a solvent) by heating the dicarboxylated intermediate (or free acid thereof) to a temperature ranging from about 140 to about 200° C.

The hydrolyzing and decarboxylating steps maybe performed at a temperature of from about 20 to about 200° C.

Suitable solvents for the alkylated phenoxy containing compound in the decarboxylating and hydrolyzing steps include, but are not limited to, organic solvents, such as ethanol, dimethylacetamide (DMAC), dimethylformamide (MDW), ketones (e.g. acetone, methylethylketone, and methylisobutylketone), and any combination of any of the foregoing.

Salts of the alkylated phenoxy containing compound may be formed by any method known in the art. For example, the acid form of the alkylated phenoxy containing compound, i.e., where the alkylated phenoxy containing compound has a —COOH moiety, may be converted into the corresponding sodium salt by reacting it with sodium hydroxide. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Sodium salts include, but are not limited to, mono-, di-, and other multi-valent sodium salts. A preferred salt is the disodium salt. The salts may also be solvates, including ethanol solvates, and hydrates. The term "solvate" as used herein includes, but is not limited to, a molecular or ionic complex of molecules or ions of a solvent, such as ethanol, with ions or molecules of the compounds of the present invention.

The present method maybe used to prepare phenoxy alkanoic, alkenoic, and alkynoic acids and salts thereof having the formula

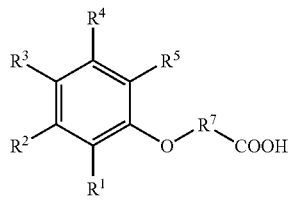

where
$R^1$, $R^2$, $R^3$, $R^4$, $R^5$, and $R^7$ are defined as above.

The alkylated phenoxy containing compounds of the present invention may be isolated and/or purified by methods known in the art. For example, the alkylated phenoxy containing compounds may be purified by recrystallization or fractionation on one or more chromatographic supports. Fractionation may be performed on suitable chromatographic supports, such as silica gel or alumina, using solvent mixtures such as acetic acid/butanol/water as the mobile phase; reverse phase column supports using trifluoroacetic acid/acetonitrile mixtures as the mobile phase; and ion exchange chromatography using water as the mobile phase. The alkylated phenoxy containing compounds may also be purified to remove impurities, such as inorganic salts, by extraction with a lower alcohol, such as methanol, butanol, or isopropanol.

The method of the present invention uses readily available and inexpensive starting materials and provides a cost-effective method for preparing and isolating alkylated phenoxy containing compounds. The method is simple to perform and is amenable to industrial scale-up for commercial production.

ACTIVE AGENT DELIVERY SYSTEMS

Dicarboxylate Delivery Agent Compounds

The dicarboxylate delivery agent compounds of the present invention include the free acids of the dicarboxylated intermediates of the present invention (i.e. when $R^8$ and $R^{11}$ are hydrogen) and salts thereof. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts, di-sodium salts, and trisodium salts. The salts may,also be solvates, including ethanol solvates, and hydrates.

The delivery agent compounds may be in the form of the free amine or salts thereof. Suitable salts include, but are not limited to, organic and inorganic salts, for example hydrochloride salts, acetate or citrate.

Salts of the delivery agent compounds of the present invention may be prepared by methods known in the art. For example, sodium salts may be prepared by dissolving the delivery agent compound in ethanol and adding aqueous sodium hydroxide. In addition, poly amino acids and peptides comprising one or more of these compounds may be used. An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids. One or more of the amino acids or peptide units may be acylated or sulfonated.

Active Agents

Active agents suitable for use in the present invention include biologically active agents and chemically active agents, including, but not limited to, pesticides, pharmacological agents, and therapeutic agents.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth honnones (rHGH), bovine growth honnones, and porcine growth hormones; growth hormone releasing hormones; growth hormone releasing factor, interferons, including $\alpha$, $\beta$ and $\gamma$, interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitinis, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-honione-releasinig-hormone; follicle stimulating hormone; glucocerebrosidase; thrombopoietin; filgrastim; prostaglandins; cyclosporin; vasopressin; cromolyn sodium (sodium or disodium chronioglycate); vancomycin; desferrioxamine (DFO); bisphosphonates, including alendronate, tiludronate, etidronate, clodronate, pamidronate, olpadronate, and incadronate; parathyroid hormone (PTH), including its fragments; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof. A preferred active agent is calcitonin and more preferably salmon calcitonin.

The composition of the present invention comprises one or more delivery agent compounds of the present invention, and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent.

Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, and any combination thereof.

The delivery agent compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the delivery agent compounds and active agents have utility in the delivery of active agents to biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as those listed in the table below, in an animal by administering the composition of the present invention. Specific indications for active agents can be found in the Physicians' Desk Reference (54th Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
| --- | --- |
| Growth hormones | Growth disorders |
| Interferons, including α, β and γ. | Viral infection, including chronic cancer and multiple sclerosis |
| Interleukin-1; interleukin-2. | Viral infection; cancer |
| Insulin; Insulin-like growth factor IGF-S1. | Diabetes |
| Heparin | Thrombosis; prevention of blood coagulation |
| Calcitonin. | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |
| Vasopressin | Bed-wetting; antidiuretic |
| Cromolyn sodium; Vancomycin | Asthma; allergies |
| Desferrioxamine (DFO) | Iron overload |

-continued

| Active Agent | Disease and Physiological Effect |
| --- | --- |
| Parathyroid hormone (PTH), including its fragments. | Osteoporosis; Diseases of the bone |
| Antimicrobials | Infection including gram-positive bacterial infection |
| Vitamins | Vitamin deficiencies |
| Bisphosphonates | Osteoporosis; Paget's disease; Inhibits osteoclasts |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent is readily assessed by measuring a known pharmacological activity in blood, e.g., an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The invention will now be illustrated in the following non-limiting example which is illustrative of the invention but is not intended to limit the scope of the invention. All percentages are by weight unless otherwise indicated.

EXAMPLE 1

A disodium salt of a phenoxy carboxylic acid compound can be prepared by the procedure shown in the flow chart below.

Alkylation

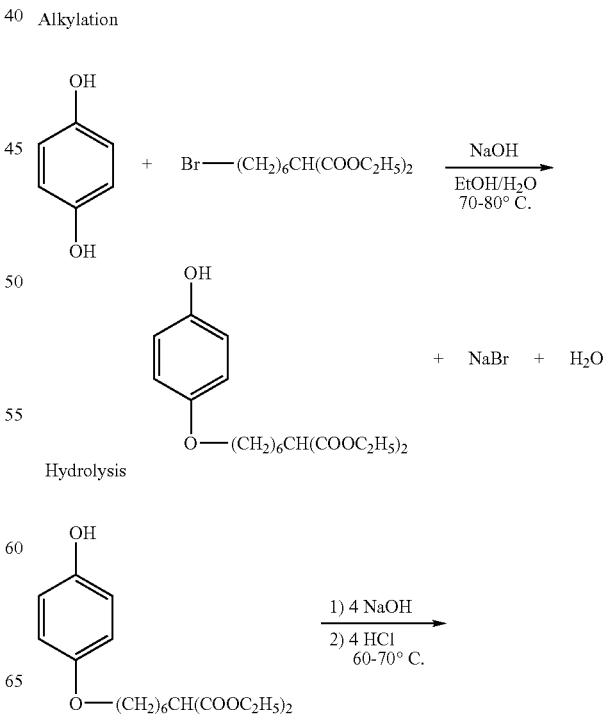

-continued

[Structure: 4-hydroxyphenyl-O-(CH$_2$)$_6$CH(COOH)$_2$]  + 3NaCl + 2EtOH + H$_2$O Decarboxylation

[Structure: 4-hydroxyphenyl-O-(CH$_2$)$_6$CH(COOH)$_2$] $\xrightarrow[\text{(reflux)}]{\text{heptane} \atop <98°\text{C.}}$ [Structure: 4-hydroxyphenyl-O-(CH$_2$)$_7$COOH] + CO$_2$ Disodium Salt Formation

[Structure: 4-hydroxyphenyl-O-(CH$_2$)$_7$COOH] + 2 NaOH $\xrightarrow[\text{20-35° C.}]{\text{EtOH/heptane}}$ [Structure: 4-NaO-phenyl-O-(CH$_2$)$_7$COONa] + 2H$_2$O All patents, patent applications, literature publications, and test methods cited herein are hereby incorporated by reference.

Many variations of the present invention will suggest themselves to those skilled in the art in light of the above detailed disclosure. All such modifications are within the full intended scope of the appended claims.

What is claimed is:

1. A method of preparing an alkylated phenoxy containing compound from a phenoxy containing compound, the method comprises the steps of (a) alkylating the phenoxy containing compound with a dicarboxylate alkylating agent to form a dicarboxylated phenoxy containing compound, and (b) decarboxylating the dicarboxylated phenoxy containing compound to form the alkylated phenoxy containing compound, wherein the dicarboxylate alkylating agent has the formula $$X-R^7 \begin{array}{c} \overset{O}{\underset{\parallel}{C}}-O-R^8 \\ \overset{\parallel}{\underset{O}{C}}-O-R^{11} \end{array}$$

wherein $R^7$ is a linear or branched $C_7$-$C_{12}$ alkylene;

$R^7$ is optionally substituted with $C_1$-$C_4$ alkyl, $C_1$-$C_4$ alkenyl, oxygen, nitrogen, sulfur, halogen, —OH, $C_1$-$C_4$ alkoxy, aryl, heteraryl, or vinyl;

$R^7$ is optionally interrupted with aryl, heteroaryl, vinyl, oxygen, nitrogen, or sulfur;

$R^8$ and $R^{11}$ are independently $C_1$-$C_4$ alkyl or $C_1$-$C_4$ haloalkyl; and X is a suitable leaving group.

2. The method of claim 1, wherein the molar ratio of phenoxy containing compound to dicarboxylate alkylating agent is from about 1:1 to about 1:0.5.

3. The method of claim 1, wherein the alkylating step is performed in the presence of a base.

4. The method of claim 3, wherein the molar ratio of base to phenoxy containing compound is greater than 1.

5. The method of claim 4, wherein the base is pyridine, picoline, tetramethylguanidine, triethylamine, diisopropylethylamine, sodium bicarbonate, potassium bicarbonate, sodium carbonate, potassium carbonate, or any combination of any of the foregoing.

6. The method of claim 5, wherein the base is sodium carbonate.

7. The method of claim 1, wherein the alkylating step is performed at a temperature of from about 40 to about 80° C.

8. The method of claim 7, wherein the alkylating step is performed at a temperature of from about 60 to about 80° C.

9. The method of claim 1, further comprising hydrolyzing one or more carboxyl moieties of the alkylated phenoxy carboxylic acid compound after step (a) to form the free acid of the alkylated phenoxy carboxylic acid compound.

10. The method of claim 9, wherein the decarboxylating step is performed after the hydrolyzing step.

11. The method of claim 1, wherein decarboxylating comprises heating the dicarboxylated phenoxy containing compound in an organic solvent to a temperature ranging from about 140 to about 200° C.

12. The method of claim 11, wherein the organic solvent has a boiling point of at least about 110° C.

13. The method of claim 11, wherein the organic solvent is selected from xylenes, toluene, heptane, dimethyl acetamide, dimethyl formamide, methyl sulfoxide, isoparaffins, and any combination of any of the foregoing.

14. A method of preparing an alkylated phenoxy containing compound from a dicarboxylated phenoxy containing compound comprising the step of decarboxylating and hydrolyzing the dicarboxylated phenoxy containing compound to form the alkylated phenoxy containing compound, wherein the dicarboxylated phenoxy containing compound has the formula

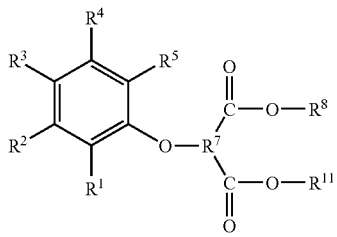

where
R$^1$, R$^2$, R$^3$, and R$^4$ are independently H, —OH, halogen, C$_1$-C$_4$ alkyl, C$_2$-C$_4$ alkenyl, C$_1$-C$_4$ alkoxy, —C(O)R$^{12}$, —NO$_2$, —NR$^9$R$^{10}$, or —N$^+$R$^9$R$^{10}$R$^{13}$ (R$^{14}$)$^-$;

R$^5$ is H, —OH, —NO$_2$, halogen, —CF$_3$, —R$^{15}$R$^{16}$, —N$^+$R$^{15}$R$^{16}$R$^{17}$ (R$^{18}$)$^-$, amide, C$_1$-C$_{12}$ alkoxy, C$_1$-C$_{12}$ alkyl, C$_2$-C$_{12}$ alkenyl, carbamate, carbonate, urea, or —C(O)R$^{19}$;

R$^7$ is a linear or branched C$_1$-C$_{20}$ alkylene, C$_2$-C$_{20}$ alkenylene, or C$_2$-C$_{20}$ alkynylene;

R$^7$ is optionally substituted with C$_1$-C$_4$ alkyl, C$_1$-C$_4$ alkenyl, oxygen, nitrogen, sulfur, halogen, —OH, C$_1$-C$_4$ alkoxy, aryl, heteraryl, or vinyl;

R$^7$ is optionally interrupted with aryl, heteroaryl, vinyl, oxygen, nitrogen, or sulfur;

R$^8$ and R$^{11}$ are independently C$_1$-C$_4$ alkyl or C$_1$-C$_4$ haloalkyl;

R$^9$, R$^{10}$, and R$^{13}$ are independently H or C$_1$-C$_{10}$ alkyl;

R$^{12}$ is H, C$_1$-C$_4$ alkyl, C$_2$-C$_4$ alkenyl, or —NH$_2$;

R$^{14}$ and R$^{18}$ are independently a halide, hydroxide, sulfate, tetrafluoroborate, or phosphate;

R$^{15}$, R$^{16}$, and R$^{17}$ are independently H, C$_1$-C$_{10}$ alkyl, C$_1$-C$_{10}$ alkyl substituted with —COOH, C$_2$-C$_{12}$ alkenyl, C$_2$-C$_{12}$ alkenyl substituted with —COOH, —C(O)R$^{20}$;

R$^{19}$ is —H, C$_1$-C$_6$ alkyl, or C$_2$-C$_{12}$ alkenyl; and

R$^{20}$ is —OH, C$_1$-C$_{10}$ alkyl, or C$_2$-C$_{12}$ alkenyl, wherein at least one of R$^1$, R$^2$, R$^3$, R$^4$ and R$^5$ is —OH or alkoxy.

15. The method of claim 1, wherein R$^7$ is a linear or branched C$_7$-C$_9$ alkylene.

16. A method of preparing an alkylated phenoxy containing compound from a phenoxy containing compound, the method comprises the steps of (a) alkylating the phenoxy containing compound with a dicarboxylate alkylating agent to form a dicarboxylated phenoxy containing compound, and (b) decarboxylating the dicarboxylated phenoxy containing compound to form the alkylated phenoxy containing compound, wherein the phenoxy containing compound has the formula

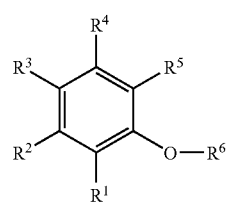

wherein
R$^1$, R$^2$, R$^3$, and R$^4$ are independently H, —OH, halogen, C$_1$-C$_4$ alkyl, C$_2$-C$_4$ alkenyl, C$_1$-C$_4$ alkoxy, —C(O)R$^{12}$, —NO$_2$, —NR$^9$R$^{10}$, or —N$^+$R$^9$R$^{10}$R$^{13}$ (R$^{14}$)$^-$;

R$^5$ is H, —OH, —NO$_2$, halogen, —CF$_3$, —R$^{15}$R$^{16}$, —N$^+$R$^{15}$R$^{16}$R$^{17}$ (R$^{18}$)$^-$, amide, C$_1$-C$_{12}$ alkoxy, C$_1$-C$_{12}$ alkyl, C$_2$-C$_{12}$ alkenyl, carbamate, carbonate, urea, or —C(O)R$^{19}$;

R$^6$ is a leaving group;

R$^9$, R$^{10}$, and R$^{13}$ are independently H or C$_1$-C$_{10}$ alkyl;

R$^{12}$ is H, C$_1$-C$_4$ alkyl, C$_2$-C$_4$ alkenyl, or —NH$_2$;

R$^{14}$ and R$^{18}$ are independently a halide, hydroxide, sulfate, tetrafluoroborate, or phosphate;

R$^{15}$, R$^{16}$, and R$^{17}$ are independently H, C$_1$-C$_{10}$ alkyl, C$_1$-C$_{10}$ alkyl substituted with —COOH, C$_2$-C$_{12}$ alkenyl, C$_2$-C$_{12}$ alkenyl substituted with —COOH, —C(O)R$^{20}$;

R$^{19}$ is —H, C$_1$-C$_6$ alkyl, or C$_2$-C$_{12}$ alkenyl; and

R$^{20}$ is —OH, C$_1$-C$_{10}$ alkyl, or C$_2$-C$_{12}$ alkenyl, wherein at least one of R$^1$, R$^2$, R$^3$, R$^4$ and R$^5$ is —OH or alkoxy.

17. The method of claim 16, wherein the dicarboxylate phenoxy containing compound has the formula

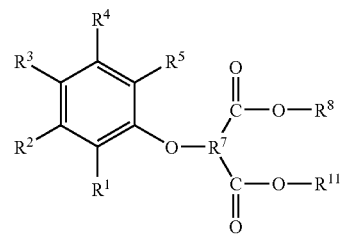

where
R$^1$, R$^2$, R$^3$, and R$^4$ are independently H, —OH, halogen, C$_1$-C$_4$ alkyl, C$_2$-C$_4$ alkenyl, C$_1$-C$_4$ alkoxy, —C(O)R$^{12}$, —NO$_2$, —NR$^9$R$^{10}$, or —N$^+$R$^9$R$^{10}$R$^{13}$ (R$^{14}$)$^-$;

R$^5$ is H, —OH, —NO$_2$, halogen, —CF$_3$, —R$^{15}$R$^{16}$, —N$^+$R$^{15}$R$^{16}$R$^{17}$ (R$^{18}$)$^-$, amide, C$_1$-C$_{12}$ alkoxy, C$_1$-C$_{12}$ alkyl, C$_2$-C$_{12}$ alkenyl, carbamate, carbonate, urea, or —C(O)R$^{19}$;

R$^7$ is a linear or branched, C$_1$-C$_{20}$ alkylene, C$_2$-C$_{20}$ alkenylene, or C$_2$-C$_{20}$ alkynylene;

R$^7$ is optionally substituted with C$_1$-C$_4$ alkyl, C$_1$-C$_4$ alkenyl, oxygen, nitrogen, sulfur, halogen, —OH, C$_1$-C$_4$ alkoxy, aryl, heteraryl, or vinyl;

R$^7$ is optionally interrupted with aryl, heteroaryl, vinyl, oxygen, nitrogen, or sulfur;

R$^8$ and R$^{11}$ are independently C$_1$-C$_4$ alkyl or C$_1$-C$_4$ haloalkyl;

R$^9$, R$^{10}$, and R$^{13}$ are independently H or C$_1$-C$_{10}$ alkyl;

R$^{12}$ is H, C$_1$-C$_4$ alkyl, C$_2$-C$_4$ alkenyl, or —NH$_2$;

R$^{14}$ and R$^{18}$ are independently a halide, hydroxide, sulfate, tetrafluoroborate, or phosphate;

R$^{15}$, R$^{16}$, and R$^{17}$ are independently H, C$_1$-C$_{10}$ alkyl, C$_1$-C$_{10}$ alkyl substituted with —COOH, C$_2$-C$_{12}$ alkenyl, C$_2$-C$_{12}$ alkenyl substituted with —COOH, —C(O)R$^{20}$;

R$^{19}$ is —H, C$_1$-C$_6$ alkyl, or C$_2$-C$_{12}$ alkenyl; and

R$^{20}$ is —OH, C$_1$-C$_{10}$ alkyl, or C$_2$-C$_{12}$ alkenyl, wherein at least one of R$^1$, R$^2$, R$^3$, R$^4$ and R$^5$ is —OH or alkoxy.

18. The method of claim 16, wherein the alkylated phenoxy containing compound has the formula

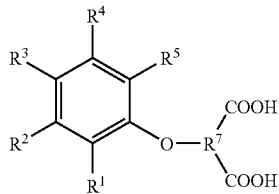

where
- $R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)$R^{12}$, —$NO_2$, —$NR^9R^{10}$, or —$N^+R^9R^{10}R^{13}$ ($R^{14}$)$^-$;
- $R^5$ is H, —OH, —$NO_2$, halogen, —$CF_3$, —$R^{15}R^{16}$, —$N^+R^{15}R^{16}R^{17}$ ($R^{18}$)$^-$, amide, $C_1$-$C_{12}$ alkoxy, $C_1$-$C_{12}$ alkyl, $C_2$-$C_{12}$ alkenyl, carbamate, carbonate, urea, or —C(O)$R^{19}$;
- $R^7$ is a linear or branched, $C_1$-$C_{20}$ alkylene, $C_2$-$C_{20}$ alkenylene, or $C_2$-$C_{20}$ alkynylene;
- $R^7$ is optionally substituted with $C_1$-$C_4$ alkyl, $C_1$-$C_4$ alkenyl, oxygen, nitrogen, sulfur, halogen, —OH, $C_1$-$C_4$ alkoxy, aryl, heteraryl, or vinyl;
- $R^7$ is optionally interrupted with aryl, heteroaryl, vinyl, oxygen, nitrogen, or sulfur;
- $R^9$, $R^{10}$, and $R^{13}$ are independently H or $C_1$-$C_{10}$ alkyl;
- $R^{12}$ is H, $C_1$-$C_4$ alkyl, $C_2$-$C_4$ alkenyl, or —$NH_2$;
- $R^{14}$ and $R^{18}$ are independently a halide, hydroxide, sulfate, tetrafluoroborate, or phosphate;
- $R^{15}$, $R^{16}$, and $R^{17}$ are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, —C(O)$R^{20}$;
- $R^{19}$ is —H, $C_1$-$C_6$ alkyl, or $C_2$-$C_{12}$ alkenyl; and
- $R^{20}$ is —OH, $C_1$-$C_{10}$ alkyl, or $C_2$-$C_{12}$ alkenyl, wherein at least one of $R^1$, $R^2$, $R^3$, $R^4$ and $R^5$ is —OH or alkoxy.

* * * * *